(12) United States Patent
Pastl

(10) Patent No.: US 11,744,624 B2
(45) Date of Patent: Sep. 5, 2023

(54) BONE SCREW

(71) Applicant: SURGEBRIGHT GMBH, Lichtenberg (AT)

(72) Inventor: Klaus Pastl, Lichtenberg (AT)

(73) Assignee: SURGEBRIGHT GMBH, Lichtenberg (AT)

(*) Notice: Subject to any disclaimer, the term of this patent is extended or adjusted under 35 U.S.C. 154(b) by 127 days.

(21) Appl. No.: 16/470,837

(22) PCT Filed: Aug. 9, 2018

(86) PCT No.: PCT/EP2018/071619
§ 371 (c)(1),
(2) Date: Jun. 18, 2019

(87) PCT Pub. No.: WO2019/034522
PCT Pub. Date: Feb. 21, 2019

(65) Prior Publication Data
US 2019/0307496 A1   Oct. 10, 2019

(30) Foreign Application Priority Data
Aug. 14, 2017   (AT) ................ A 50672/2017

(51) Int. Cl.
*A61B 17/86* (2006.01)
*A61B 17/88* (2006.01)

(52) U.S. Cl.
CPC .......... *A61B 17/862* (2013.01); *A61B 17/866* (2013.01); *A61B 17/8625* (2013.01); *A61B 17/8883* (2013.01)

(58) Field of Classification Search
CPC .. A61B 17/86–17/8685; F16B 23/0007; F16B 23/003; F16B 23/0061
See application file for complete search history.

(56) References Cited

U.S. PATENT DOCUMENTS 3,584,667 A * 6/1971 Reiland ................ F16B 23/003
  81/460
3,969,974 A * 7/1976 Lejdegard ............ F16B 23/003
  411/405

(Continued)

FOREIGN PATENT DOCUMENTS

WO  00/66011  11/2000

OTHER PUBLICATIONS

Int'l Search Report conducted in Int'l Appln. No. PCT/EP2018/071619 (dated Nov. 23, 2018).

(Continued)

*Primary Examiner* — Zade Coley
(74) *Attorney, Agent, or Firm* — Greenblum & Bernstein, P.L.C.

(57) ABSTRACT

Bone graft comprising cortical bone material having a screw shank with an external thread and a screw head. Screw head has an outer jacket surface which is rotationally symmetrical about a screw head axis and has an external thread. At least two recesses, which are distributed about the screw head axis, extend axially in the direction of the screw head axis and open into an end face of a free end of the screw head, for receiving an insertion tool. The recesses are each formed by side faces, which extend from the outer jacket surface in the direction of the screw head axis and merge into one another in a surface section close to the axis. By this design, introduction of an insertion torque is optimized and new surgical areas of application such as in intramedullary splinting, arthroscopic insertion and deep insertion of the graft into an bearing bone are possible.

10 Claims, 3 Drawing Sheets

(56) References Cited

U.S. PATENT DOCUMENTS

| | | | | |
|---|---|---|---|---|
| 5,279,190 | A * | 1/1994 | Goss | F16D 3/20 81/460 |
| 5,378,101 | A * | 1/1995 | Olson | B25B 13/485 411/404 |
| 5,762,457 | A * | 6/1998 | Lide | B25B 13/065 411/405 |
| 6,045,554 | A * | 4/2000 | Grooms | A61B 17/862 606/304 |
| 6,269,716 | B1 * | 8/2001 | Amis | F16B 23/003 411/410 |
| 6,357,981 | B1 * | 3/2002 | Lanham | F16B 23/0061 411/374 |
| 6,875,215 | B2 * | 4/2005 | Taras | A61B 17/1637 606/312 |
| 7,182,781 | B1 * | 2/2007 | Bianchi | A61F 2/446 623/17.11 |
| 7,479,010 | B2 * | 1/2009 | Levisman | A61C 8/0018 433/174 |
| 7,846,167 | B2 * | 12/2010 | Garcia | A61B 17/862 606/104 |
| 8,523,914 | B2 * | 9/2013 | Foley | A61B 17/7032 606/265 |
| 9,593,707 | B2 * | 3/2017 | Weis | B60B 7/14 |
| 10,278,748 | B2 * | 5/2019 | Aebi | A61B 17/846 |
| 2001/0007074 | A1 * | 7/2001 | Strobel | A61B 17/8877 606/305 |
| 2002/0052605 | A1 * | 5/2002 | Grooms | A61B 17/8891 606/280 |
| 2003/0028193 | A1 * | 2/2003 | Weil | A61B 17/863 606/304 |
| 2003/0158556 | A1 * | 8/2003 | Taras | A61B 17/8883 606/916 |
| 2004/0149088 | A1 * | 8/2004 | Yamamoto | B25B 13/065 81/121.1 |
| 2007/0106283 | A1 * | 5/2007 | Garcia | A61B 17/8883 606/1 |
| 2007/0274800 | A1 * | 11/2007 | Mikkonen | A61B 17/8891 411/15 |
| 2008/0132959 | A1 * | 6/2008 | Mikkonen | A61B 17/8685 606/308 |
| 2008/0300639 | A1 * | 12/2008 | Martin | A61B 17/863 606/315 |
| 2011/0182696 | A1 * | 7/2011 | Ogawa | F16B 23/0061 411/404 |
| 2011/0314768 | A1 * | 12/2011 | Johnson | F16B 12/14 52/745.21 |
| 2012/0029577 | A1 * | 2/2012 | Kerr | A61B 17/8883 606/305 |
| 2012/0078300 | A1 * | 3/2012 | Mayer | A61B 17/0401 606/232 |
| 2013/0129447 | A1 * | 5/2013 | Canizares, Jr. | B25B 15/005 411/407 |
| 2017/0258503 | A1 * | 9/2017 | Aebi | A61B 17/846 |

OTHER PUBLICATIONS

Austria Office Action conducted in Austria Appln. No. 1B A 50672/2017 (dated Feb. 13, 2018) (w/ machine translation).

* cited by examiner

BONE SCREW

The invention relates to a bone graft made of a cortical bone material having a screw shank which is provided with an external thread and a screw head for initiating a torque, according to the preamble of claim 1.

Screws for surgical osteosynthesis are conventionally made of metal or metal alloys. Screws made of resorbable material, such as polyglycolide and polylactide, are also known. However, screws of this type have several disadvantages in surgical practice. Fox example, screws made of metal or metal alloys have to be removed by a second operation on the one hand and are subject to changes due to corrosion on the other. This increases the costs in the health system as well as the health risks for each patient through a new operation. Most bone fractures are treated surgically with a plate and a large number of screws that have to be removed later.

All resorbable materials in the human or animal body form a or less solid bridge between the bones to be osteosynthesized depending on the material but are dissolved, which has a negative effect on the strength of the osteosynthesis of the affected bones. Furthermore, some resorbable synthesis materials lead to large osteolyses in the surrounding bone during their degradation, i.e. the recipient bone moves away from the screw.

Allogeneic bone screws (femur and tibia corticalis), on the other hand, offer several advantages. They are vascularized and remodeled without rejection and are particularly suitable for osteosynthesis where small bone fragments have to be joined together since the screw already creates a load-bearing bone bridge during the operation, which improves from the time of the operation by remodeling itself and being fully integrated and incorporated into the living bone. Screws with a diameter of 3-4 mm, for example, are completely grown through with vessels within 2 months. These bone screws can therefore also be referred to as bone grafts. In contrast, metal screws are more of an obstacle to new bone formation, in particular by their mere presence they reduce the surface available for bone healing. Degradable materials in turn have their maximum strength at the time of surgery. They have the same disadvantages as the metal screws, and their strength decreases rapidly as the degradation process begins, causing the bone to be osteosynthesised to weaken, at least temporarily.

In addition, a second operation to remove the osteosynthesis material is not necessary for bone screws made of allogeneic bone, since the bone is completely converted into its own bone (not resorbed!). This reduces the risk of surgery for the patient and inevitably reduces the costs for the healthcare system. Screws made of allogeneic bone do not interfere with imaging procedures, unlike metal screws, which leave interfering artifacts in the MRI and CT. Follow-up examinations are also possible without any problems and allow a better evaluation of the healing success. Therefore, screws made of bone material are also suitable to be completely countersunk in the bone, for example in the context of an intramedullary placement of the screw in the medullary cavity, for example of tubular bone.

However, when using screws made of allogeneic bone in surgical practice, it must be noted that they differ considerably from metal screws in terms of insertion resistance and strength. Since they are derived from allogeneic, human corticalis, it is not to be expected that knowledge about thread forms, insertion resistance or strength as known from metal screws is easily transferable. In fact, this is one reason why screws made of autologous or allogeneic bone have not yet been used in surgical practice.

In addition, in the case of screws made of cortical bone material it has proven to be much more difficult to manufacture tension or compression screws, especially with self-tapping threads. Tension or compression screws pull the two bone parts to be connected towards each other as they are screwed in. For this purpose, the surgeon inserts the screw into a prefabricated hole, which is advantageously equipped with a self-tapping thread, wherein, after passing through the first bone part and entering the second bone part, the screw presses the two bone parts together. If the screw does not have a self-tapping thread, a thread must first be pre-cut into the prefabricated hole before the screw can be screwed in. The use of screws made of bone material has not yet been widespread, not least because the manufacture of tension or compression screws, especially with self-tapping threads, was considered impossible because the required insertion torque could not be guaranteed.

It is therefore the object of the invention to improve screws made of cortical bone in such a way that the maximum possible insertion torque is increased and an optimal strength of the bone connection is achieved. In particular, applications such as the fabrication of a tension or compression screw or the fabrication of an intramedullary splint are to be facilitated.

These objects are achieved by the features of claim 1. Claim 1 relates to a bone graft made of cortical bone material with a screw shank provided with a thread and a screw head to induce a torque. According to the invention, it is proposed that the screw head has an outer jacket surface which is rotationally symmetrical about a screw head axis and which is provided with an external thread, as well as at least two outer recesses for receiving an insertion tool, which recesses are distributed around the screw head axis, extend axially in the direction of the screw head axis and open into the end face of the free end of the screw head, wherein the recesses each are formed by side faces which extend from the outer jacket surface in the direction of the screw head axis and merge into one another in a surface section close to the axis.

In accordance with the invention, the screw head is also provided with an external thread and thus contributes to the strength of the bone connection. In particular, the screw head can also be screwed into the bone, for example within the framework of an intramedullary splint, without having to be cut off. The external thread is only interrupted by the axially extending recesses provided for the initiation of a torque in accordance with the invention, the side faces of which extend from the outer jacket surface in the direction of the screw head axis and merge into one another in a surface section close to the axis. The bone graft is otherwise free of drilling and consists entirely of bone material. Bone material thus remains in the area of the screw head axis in particular; only axial recesses are milled into the outer jacket of the screw head, which lead into the proximal end face of the screw head. The axial length of the axial recesses is at least as large in value as the diameter of the screw head in this area. Axial extensions of an insertion tool can be inserted axially into these recesses on the face side. The insertion torque is then applied to the side surfaces of the recesses. However, due to the design of the screw head according to the invention, the maximum insertion torque can be increased, since the strength of the screw head is increased by removing as little bone material as possible. In addition, the insertion torque is applied in a kinematically favorable manner in the outer circumferential area of the screw head.

In this way, the maximum insertion torque can be increased sufficiently to allow the use of bone screws as tension or compression screws. In addition, the applicant was able to demonstrate that even the design of a self-tapping thread for use in the cancellous bone region is possible and that the bone screw made of cortical bone material is thus able to be used in the cancellous bone without having to pre-cut a thread in the cancellous bone beforehand.

The insertion torque can also be increased by convexly designing the side surfaces of the recesses extending from the outer surface in the direction of the screw head axis and by designing the surface section close to the axis in a concave manner. In this way, the contact surface for the extensions of the insertion tool and the remaining amount of bone in the screw head can be increased. Both increase the insertion torque. In addition, the bone surface in the area of the screw head is enlarged and the ingrowth into the bearing bone is improved.

In addition, to increase the insertion torque, it is proposed that four recesses are provided, arranged symmetrically around the screw head axis. In the course of the axial insertion of the extensions of the insertion tool, in the case of four recesses arranged symmetrically around the screw head axis with the usual diameters for bone screws in the single-digit millimeter range, the screw head areas remaining between the recesses are gripped by the extensions of the insertion tool and "clamped", so to speak, whereby the breaking off of bone material is prevented.

Furthermore, in accordance with a preferred embodiment, it is proposed that the recesses at their axial end facing away from the end face should have an area in which the depth of the recesses measured in the radial direction is continuously reduced. If axial extensions of an insertion tool are inserted axially into the recesses, these areas of reduced depth form a frictional connection to the extensions in addition to the positive connection formed between the recesses and extensions, thereby increasing the coupling forces. In this way, an endoscopic or arthroscopic insertion of the screw is also possible. A further advantage of this design is that the fabrication of the bone screw is made much easier since it has to be sterilized during fabrication and is subject to a slight shrinkage, which could impair the tight fit to the insertion tool. Due to the additional frictional connection, high coupling forces can be guaranteed, even if the bone material has shrunk during sterilization.

For designing a tension or compression screw, it is proposed that the external thread extending over the screw shank and screw head has two sections with different thread pitches. These two sections are each located in the bone areas to be connected. Due to the different thread pitch, the bone areas to be connected are pressed together at a certain angle of rotation, which is of course the same for both sections.

For designing a screw with self-tapping thread, it is proposed that the external thread extending over the screw shank and screw head has two sections with different external thread diameters. The screw head is located in the area with the larger outer diameter of the thread. With such a screw, a core hole for the larger outer thread diameter in a first bone part can first be prefabricated during the course of operative osteosynthesis, and through the larger core hole a core hole for the smaller outer thread diameter in a second bone part that is to be connected to the first bone part can be made. The screw can now be inserted with the section with the smaller outer thread diameter through the core hole for the larger outer thread diameter until it can be screwed into the core hole of the second bone part without first having to cut a thread into the respective core hole. Subsequently, the screw enters the core hole of the first bone part with its section with a larger outer thread diameter and automatically cuts the thread there.

Due to the design of the screw head according to the invention, the introduction of the torque is optimized, i.e. the transmission of the torque exerted on the screw head via an insertion tool. The recesses according to the invention also allow the outer diameter of the screw head to be aligned with the outer diameter of the screw shank and with the outer diameter of the insertion tool, thus enabling new surgical applications such as in the field of intramedullary splinting or during arthroscopic use. Another major advantage is that the screw graft can be countersunk to any bone depth. The external thread diameter of the bone graft is preferably between 7.0 mm and 4.5 mm. The length of the bone graft is at least three times the diameter of the bone graft in the case of a cylindrical design and at least three times the largest diameter of the bone graft in the case of a frusto-conical design thereof.

Depending on the surgical application, the bone graft can be cylindrical or shaped in the manner of a truncated cone. A truncated cone-shaped design will be advantageous, for example, if the bone graft is used as a thread anchor. Thread anchors are used for the refixation of soft tissue, in particular for the refixation of tendons to bone. Medical thread anchors usually have an anchor body that is driven into a bone to attach the thread anchor. For this purpose, a thread is formed on the anchor body so that the thread anchor can be screwed into the bone. In addition, these thread anchors have at least one thread guide which serves as a holder and guide for a thread, by means of which the soft tissue is attached to the thread anchor and thus also to the bone. In the conventional way, the thread guide is formed by an opening extending transversely to the longitudinal axis of the thread anchor. One or more threads are threaded into this aperture in such a way that the two ends of a thread are guided proximal to the outside of the peripheral side of the thread anchor at the two openings of the aperture. Conventional thread anchors are made of titanium or bioresorbable materials such as polylactide and show major disadvantages in practical use, especially due to osteolytic processes and inflammatory processes. Osteolytic processes can lead to loosening and finally to the implant breaking out. Bioresorption, on the other hand, is a process that takes years and can be accompanied by inflammation and pain. Using a bone graft according to the invention as a thread anchor avoids such disadvantages. For this purpose, it is first suggested that the shank of the screw has an end face perpendicular to the axis of the screw head on its free end facing away from the screw head. This free end, facing away from the screw head, is thus the distal end of the screw, which is inserted into a prefabricated hole during surgical application. Furthermore, it is proposed that this end face of the screw shank, which is perpendicular to the axis of the screw head, be provided with a groove crossing the end face, which opens on its opposite sides in each case into the outer jacket surface of the screw shank. This groove represents the thread guide, into which a thread can be inserted during surgical application as a thread anchor and guided proximally along the outer surface before the bone graft is screwed into the prefabricated bore using a screwing tool. For this purpose, the bone graft has at its proximal end the screw head with the recesses according to the invention for accommodating the insertion tool.

The bone graft according to the invention can also be used in a similar way as a tendon anchor for the refixation of tendons to bone. The bone graft according to the invention is screwed into a prefabricated bore with the aid of an insertion tool, wherein the end of the tendon is fastened by frictional connection between the prefabricated bore and the inserted bone graft. First experiments by the applicant show that the strength of the tendon anchor is superior to that of conventional tendon anchors. The bone graft according to the invention is designed as a suppository for this purpose and thus has a cylindrical section proximally which converges distally into a conical section. The external thread extends at least over the cylindrical section. At its proximal end, the cylindrical section has the screw head with the recesses for the insertion tool according to the invention.

The invention is explained in more detail below using embodiment examples with the help of the enclosed figures, wherein.

Figure 4:
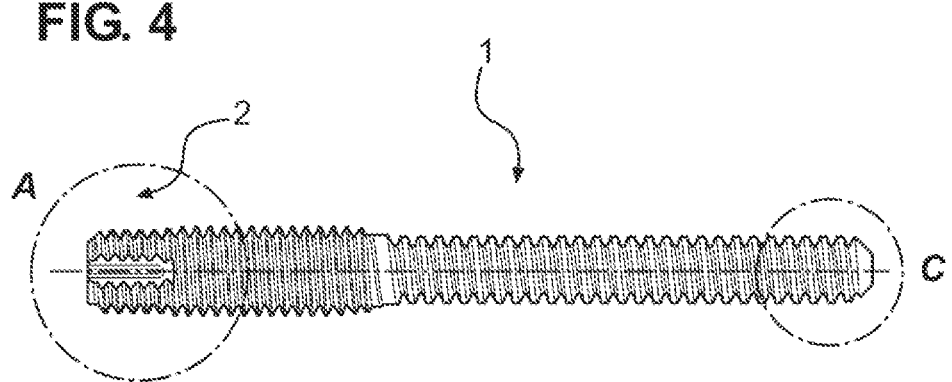
Figure 5:
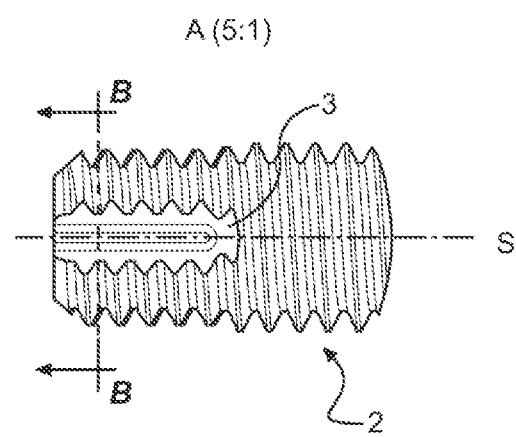
Figure 6:
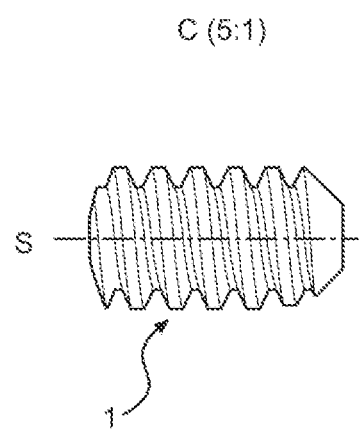
Figure 7:
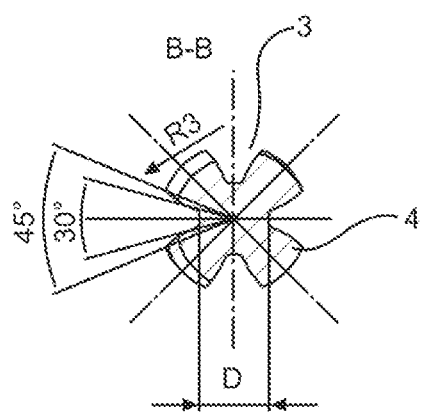
Figure 8:
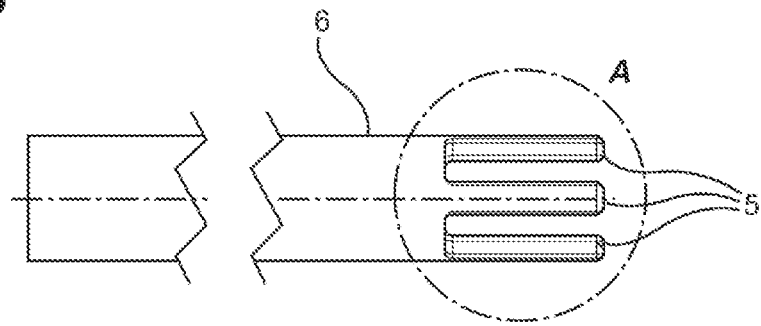
Figure 9:
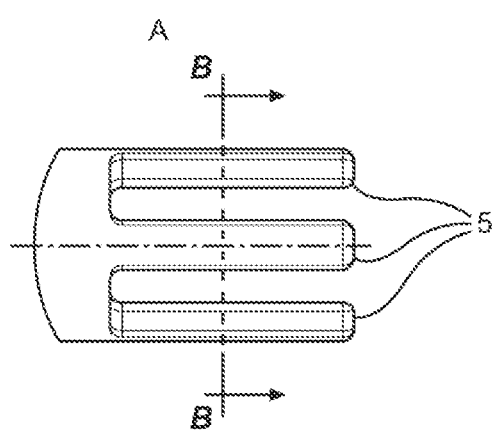
Figure 10:
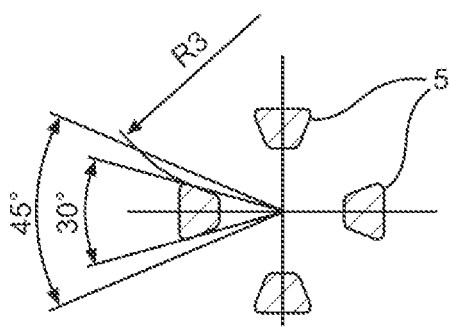

FIG. 4 an embodiment of another embodiment of a bone graft according to the invention, FIG. 5 shows the detail A of FIG. 4, FIG. 6 shows the detail C of FIG. 4, FIG. 7 shows a cross-section along the section plane B-B of FIG. 5, FIG. 8 shows a side view of an embodiment of an insertion tool for a bone graft according to the invention, FIG. 9 shows the detail A of FIG. 8, and the FIG. 10 shows a cross-section along the section plane B-B of FIG. 9.

Figure 1:
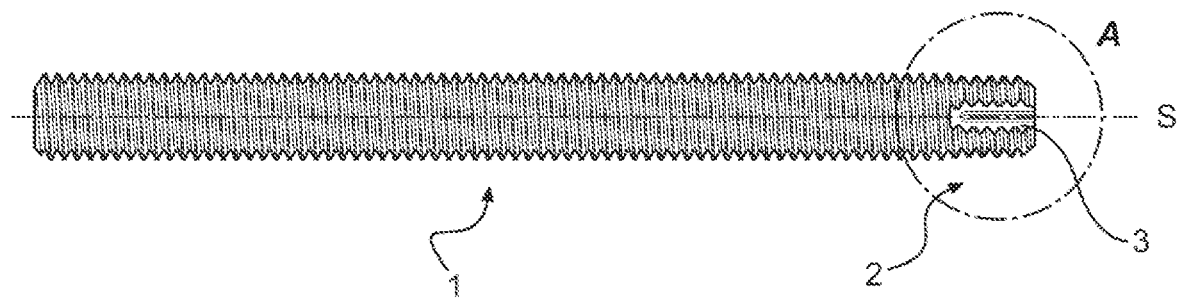
FIG. 1 shows an embodiment of a bone graft according to the invention.
Figure 2:
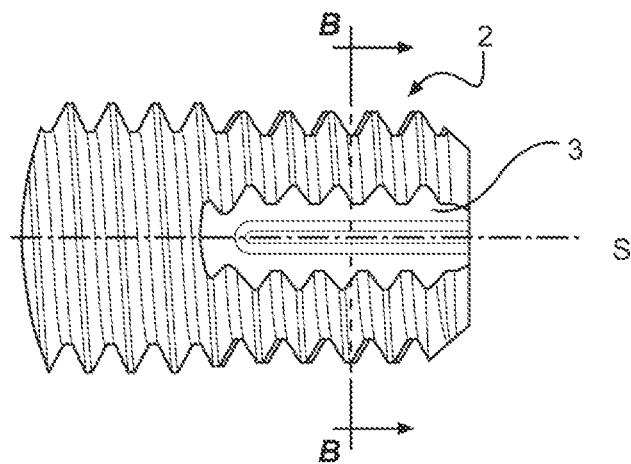
FIG. 2 shows the detail A of FIG. 1.
Figure 3:
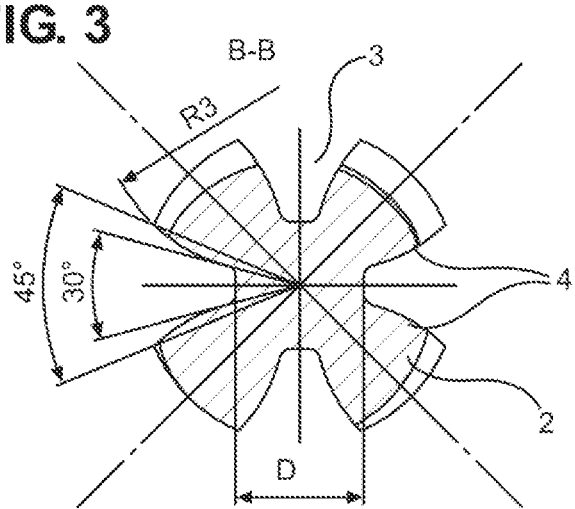
FIG. 3 shows a cross-section along the section plane B-B of FIG. 2.

First, FIGS. 1 to 3 are discussed, which show a first embodiment of a bone graft made of cortical bone material for surgical osteosynthesis. The bone graft has a cylindrical screw shank 1 provided with an external thread and a screw head 2 to induce a torque, which also heals and does not have to be cut away like conventional screw heads. The screw head 2 also has an outer jacket surface which is rotationally symmetrical about a screw head axis S and which is also provided with an external thread, as well as four recesses 3, which are distributed about the screw head axis S, extend axially in the direction of the screw head axis S and open into the end face of the free end of the screw head 2, for receiving an insertion tool (see FIGS. 2 and 3). The axially extending recesses 3 are each formed by side surfaces 4 extending from the outer shell surface in the direction of the screw head axis S, which merge into one another in a surface section close to the axis (see FIG. 3). At their axial end facing away from the end face, the recesses 3 have an area in which the depth of the recesses 3 measured in the radial direction is continuously reduced (see FIG. 2). As can be seen in particular from FIG. 3, the side surfaces 4 of the recesses 3 extending from the outer circumferential surface in the direction of the screw head axis S are formed in a convex manner, and the surface section close to the axis is concave.

As shown in FIGS. 1 to 3, the external thread extends with unchanged thread parameters both over the screw shank 1 and over the screw head 2. The screw head 2 thus contributes to the strength of the bone connection. In particular, the screw head 2 can also be screwed into the bone, for example within the framework of an intramedullary splint, without having to be cut off. The external thread is only interrupted by the axially extending recesses 3 provided for the introduction of a torque. Bone material with a core diameter D remains in the area of the screw head axis S, as shown in FIG. 3, since only axial recesses 3 are milled into the outer jacket surface of the screw head 2, which open into the end face of the screw head 2. Axial extensions 5 of an insertion tool 6 (see FIG. 8) can be inserted axially into these recesses 3 on the face side. The insertion torque is then applied to the side faces 4 of the recesses 3. Due to the design according to the invention of screw head 2, however, the maximum final torque can be increased, since the strength of screw head 2 is increased by removing as little bone material as possible. In addition, the insertion torque is applied in a kinematically favorable manner in the outer circumferential area of the screw head 2. In this way, the maximum insertion torque can be increased sufficiently to allow the use of bone screws as tension or compression screws. In addition, even a self-tapping thread can be used in the cancellous bone area, so that the bone screw made of cortical bone material is able to be used in the cancellous bone without first cutting a thread in the cancellous bone.

FIGS. 4 to 7 show a further embodiment of a bone graft according to the invention in which the external thread extending over screw shank 1 and screw head 2 has two sections with different thread pitches and external thread diameters. The screw head 2 is located in the area with the larger outer thread diameter, which for example has a thread pitch of 0.8 mm. The area with the smaller outer thread diameter, for example, has a thread pitch of 1 mm. Such an embodiment is particularly suitable for the design of a tension or compression screw. In their surgical application, the two sections are each located in the bone areas to be connected. Due to the different thread pitch, the bone areas to be connected are pressed together at a certain angle of rotation, which is of course the same for both sections.

To make a screw with self-tapping thread, it is proposed that the external thread extending over screw shank 1 and screw head 2 has two sections with different external thread diameters. With such a screw, a core hole for the larger outer thread diameter in a first bone part can first be prefabricated during the course of operative osteosynthesis, and through the larger core hole a core hole for the smaller outer thread diameter in a second bone part that is to be connected to the first bone part can be made. The screw can now be inserted with the section with the smaller outer thread diameter through the core hole for the larger outer thread diameter until it can be screwed into the core hole of the second bone part without first having to cut a thread into the respective core hole. Subsequently, the screw enters the core hole of the first bone part with its section with a larger outer thread diameter and automatically cuts the thread there.

FIGS. 8 to 10 show a possible embodiment of an insertion tool for the bone graft according to the invention. It has four axially protruding extensions 5 from a cylindrical shaft, which can be inserted axially into the recesses 3 of the bone graft on the front side until they engage in the recesses 3 with a large frictional connection. The frictional connection is increased by the side surfaces 4 of the recesses 3 extending convexly from the outer jacket surface in the direction of the screw head axis S, as well as by the depth of the recesses 3 continuously decreasing in the radial direction at their axial end facing away from the end surface.

Due to the design of the screw head 2 according to the invention, the introduction of the torque is optimized, i.e. the transmission of the torque exerted via an insertion tool to the screw head 2. The recesses 3 according to the invention also allow the outer diameter of the screw head to be aligned with the outer diameter of the screw shank 1 and with the outer diameter of the insertion tool, thus enabling new surgical applications such as in intramedullary splinting.

The invention claimed is:

1. A bone graft comprising:
a screw shank provided with an external thread;
a screw head configured for introducing a torque;
the screw shank and the screw head comprising a cortical bone material;
the screw head having an outer jacket surface rotationally symmetrical about a screw head axis;
the screw head comprising an external thread and at least two recesses distributed about the screw head axis;
the screw head having a free end with an end face;
the at least two recesses of the screw head extending axially in a direction of the screw head axis and open into the end face of the free end of the screw head to thereby be configured to receive an insertion tool for endoscopic or arthroscopic insertion of the screw;
each of the recesses being formed by side surfaces that extend from the outer jacket surface in a direction toward the screw head axis and merge into one another in a surface section close to the screw head axis, with each of the recesses as seen in the direction of the screw head axis having an inner radial section being formed by the side surfaces that extend in a radial direction below the thread and an outer radial section being formed by the side surfaces that extend in a radial direction into the thread region, and the radial depth of the inner radial section being larger than the radial height of the outer radial section.

2. The bone graft according to claim 1, wherein:
the side surfaces of the recesses extending from the outer surface in the direction of the screw head axis are of convex design, and the surface section merging close to the axis is of concave design.

3. The bone graft according to claim 1, wherein:
the at least two recesses comprise four recesses that are distributed symmetrically about the screw head axis.

4. The bone graft according to claim 1, wherein:
each of the recesses have, at a respective axial end remote from the end face, a region in which a depth of the recesses measured in the radial direction is continuously reduced.

5. The bone graft according to claim 1, wherein:
the external thread extending over the screw shank and screw head has two sections of different thread pitch.

6. The bone graft according to claim 1, wherein:
the external thread running via the screw shank and screw head-has two sections with different external thread diameters.

7. The bone graft according to claim 1, wherein:
the screw shank is of cylindrical design.

8. The bone graft according to claim 1, wherein:
the screw shank is of frustoconical design.

9. The bone graft according to claim 1, wherein:
the screw shank has on a free end remote from the screw head an end face perpendicular to the screw head axis.

10. The bone graft according to claim 9, herein:
the end face of the screw shank perpendicular to the screw head axis is provided with a groove that crosses the end face and that opens respectively on opposite sides into the outer jacket surface of the screw shank.

* * * * *